United States Patent [19]

Berner et al.

[11] Patent Number: 4,675,330
[45] Date of Patent: Jun. 23, 1987

[54] PLEUROMUTILIN DERIVATIVES PROCESS FOR THEIR PREPARATION AND THEIR USE

[75] Inventors: Heinz Berner; Hermann Vyplel, both of Vienna, Austria

[73] Assignee: Sandoz Ltd., Basil, Switzerland

[21] Appl. No.: 860,266

[22] Filed: May 6, 1986

Related U.S. Application Data

[63] Continuation of Ser. No. 700,611, Feb. 11, 1985, abandoned.

[30] Foreign Application Priority Data

Feb. 17, 1984 [DE] Fed. Rep. of Germany ....... 3405632
Apr. 12, 1984 [DE] Fed. Rep. of Germany ....... 3413708

[51] Int. Cl.$^4$ .................. A01N 31/06; C07D 277/06; C07D 207/09; C07D 149/23
[52] U.S. Cl. .................... 514/365; 514/423; 514/550; 548/200; 548/537; 560/153
[58] Field of Search ................ 548/200, 537; 560/153; 514/365, 423, 550

[56] References Cited

U.S. PATENT DOCUMENTS 3,919,290 11/1975 Egger et al. ........................ 560/153
4,060,542 11/1977 Riedl ............................ 560/190 X
4,086,359 4/1978 Dursch ........................... 560/153 X
4,107,434 8/1978 Waldvogel ....................... 560/153 X
4,390,558 6/1983 Ridgeway et al. ............. 514/550 X

FOREIGN PATENT DOCUMENTS 2121035A 12/1983 United Kingdom ................ 560/153

OTHER PUBLICATIONS

Egger, et al., The Journal of Antibiotics, vol. 29; pp. 923–927 (1976).
Schuster, et al., Cytocbrome P-450, Biochem., Biophys., Implic., (1982), pp. 555–558.

*Primary Examiner*—Joseph Paul Brust
*Attorney, Agent, or Firm*—Gerald D. Sharkin; Richard E. Vila; Frederick H. Weinfeldt

[57] ABSTRACT

A compound of formula I

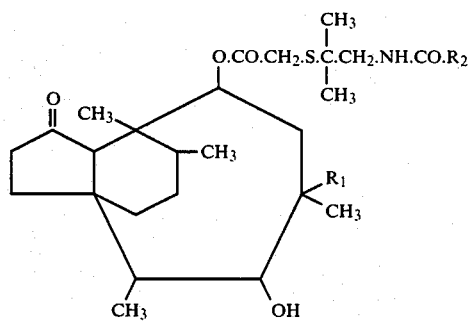

wherein
  $R_1$ represents ethyl or vinyl and
  $R_2$ represents a five membered saturated heterocycle or aminoalkyl unsubstituted or substituted in its alkyl moiety by hydroxy, in free or in the form of an acid addition or quaternary salt, which compounds are indicated for use as chemotherapeutic agents e.g. as anti-bacterially active antibiotics and as veterinary agents e.g. in combatting microorganism infections and promoting growth in domestic animals.

20 Claims, No Drawings

PLEUROMUTILIN DERIVATIVES PROCESS FOR THEIR PREPARATION AND THEIR USE

This is a continuation of application Ser. No. 700,611, filed Feb. 11, 1985, now abandoned.

The present invention concerns derivatives of 14-0-[(1-Amino-2-methylpropan-2-yl)thioacetyl]-mutilin and -19,20-dihydro-mutilin. In particular it concerns an N-Acyl-14-0-[(1-amino-2-methylpropan-2-yl)thioacetyl]-mutilin or -19,20-dihydro-mutilin.

More particularly the invention concerns compounds of formula I

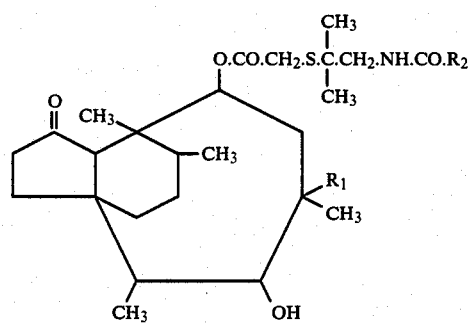

wherein
$R_1$ represents ethyl or vinyl and
$R_2$ represents a five membered saturated heterocycle or aminoalkyl unsubstituted or substituted in its alkyl moiety by hydroxy,
in free form or in the form of an acid addition or quaternary salt.

The compounds of the invention may be obtained by acylating 14-0-[(1-Amino-2-methylpropan-2-yl)thioacetyl]mutilin or -19,20-dihydromutilin and more particularly by reacting a compound of formula II

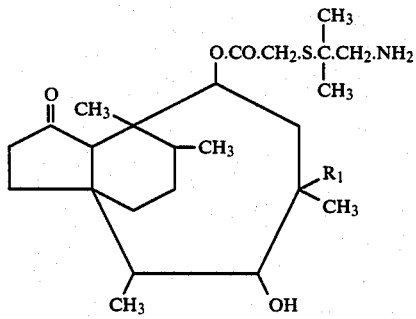

with a reactive ester of a compound of formula III

whereby $R_2'$ has the same meaning as $R_2$ above except that any amino groups present therein are protected, deprotecting any protected amino groups and recovering the compound thus obtained in free form or in the form of an acid addition salt or a quaternary salt.

This process according to the invention can be carried out by dissolving or suspending a compound of formula II and a compound of formula III in a solvent inert under the reaction conditions e.g. in a di(lower)alkylcarboxylic acid amide such as dimethylformamide, and allowing the reaction to proceed at room temperature or at a raised temperature preferably at room temperature. The subsequent splitting-off of protecting groups can be carried out according to conventional methods for example by reductive deprotection with Pd/active charcoal and hydrogen or by treatment with trifluoroacetic acid. The final products can be isolated from the reaction mixture and if necessary purified according to conventional methods.

The compounds of formula I can be converted into their acid addition salts and vice versa in conventional manner. Corresponding quaternary salts can be obtained from the compounds of formula I in conventional manner.

The compounds of formula I may contain at least one asymmetric carbon atom and may thus exist in the form of diastereomeric isomers and mixtures thereof which may be separated in conventional manner. Use of optically active starting materials will lead to the corresponding end products. The invention concerns both isomers and mixtures thereof and reference is made to the latter unless otherwise stated.

The compounds of formula I exhibit interesting biological in particular chemotherapeutical activity and are therefore useful as medicaments. They display an inhibitory activity against bacteria as determined in tests in vitro with the series dilution test using various bacterial strains e.g. Staph. aureus, Staph. epidermidis, Strept. pyogenes, Strept. pneumoniae, E. coli, Klebsiella pneumoniae, Haemophilus spp., Leptospiren spp., Erysipelothrix rhusiophathiae and obligatory anaerobes, e.g. Bacteroides fragilis from a concentration of ca. 0.008 to 25 $\mu$g/ml. In particular an inhibitory activity was also found against Mycoplasms and Chlamydia which exhibits itself from a concentration of ca. 0.008 to 0.5 $\mu$g/ml. The chemotherapeutic activity of the compounds was established through tests on mice, using various bacterial strains, and on hens, using mycoplasma strains. This inhibitory activity was observed from a concentration of ca. 12 to 50 mg/kg of body weight. The compounds according to the invention can therefore be used as anti-bacterially active antibiotics.

In addition the above mentioned compounds display an anti-parasitic activity, in particular against coccidia as well as a growth promoting activity. To establish the activity against coccidia testing took place in vivo on the hen. The activities can be confirmed in these animal tests at dosages of 20–150 mg/kg of feed depending upon the period of application. The growth promoting properties were established in hen and pig in a dosage range of 10–50 mg/kg feed. The compounds of formula I are therefore suitable as veterinary agents in particular for the chemotherapeutic treatment of coccidioses in fowl as well as growth promoters in the animal species mentioned.

In use, the effective dosage will, of course, vary depending on the particular compound employed, the mode of administration and the treatment desired. However, in general, satisfactory results as anti-baterials and anti-anaerobics can be obtained when the compounds are administered at a daily dosage of from about 10 to 300 mg/kg of animal body weight, suitably given in divided doses two to four times daily. For most large mammals, the total daily dosage is from about 1 g to 3 g, and dosage forms suitable for internal administration comprise about 250 to 1500 mg of the compound in admixture with a solid or liquid pharmaceutical carrier or diluent.

For the prophylaxis or therapy of microorganism infections and for growth promotion in domestic animals, the dosage will of course vary depending upon the size and age of the animal and the effect desired; for example for prophylactic treatment relatively low doses would be administered over a long time. Preferred doses in drinking water are from 0.0125 to 0.05 weight by volume, particularly 0.0125 to 0.025, and in foodstuffs from 20 to 400 g/metric ton, particularly 20 to 200 g/metric ton. It is preferred to administer the active compound to hens in drinking water, and to pigs in the foodstuff.

The compounds may be used in free base form or in the form of chemotherapeutically/physiologically acceptable acid addition and quaternary salts. Such salt forms exhibit the same order of activity as the free base forms.

Examples of suitable acid addition salts are the hydrogen fumarate, fumarate, naphthalin-1,5-sulphonate and especially the hydrochloride.

The compounds may be administered orally, locally or parenterally and admixed with conventional chemotherapeutically acceptable diluents and carriers, and, optionally, other excipients and administered in such forms as tablets, capsules or injectable preparations.

The compounds also form excellent additives for feed mixes (as premix) or for drink water as well as for diluting fluids for artificial insemination and for egg-dipping techniques.

Such compositions also form part of the invention.

The invention therefore also concern a method of combatting bacteria and obligatory anaerobes comprising administering to a subject in need of such treatment an effective amount of a compound of formula I or a chemotherapeutically acceptable acid addition or quaternary salt thereof and such compounds for use as chemotherapeutic agents, in particular anti-bacterially active antibiotics and agents against infections caused by obligatory anaerobes.

The invention further provides a method of combatting microorganism infections and promoting growth in domestic animals which comprises administering to a subject in need of such treatment an effective amount of a compound of formula I or a physiologically acceptable acid addition or quaternary salt thereof and such compounds for use in combatting coccidia and promoting growth in domestic animals.

The starting materials of formula II are new and may be obtained by reacting a compound of formula IV

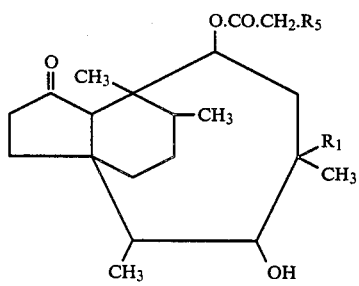

wherein $R_1$ is as defined above and $R_5$ stands for chlorine, bromine or a $O.SO_2.R_6$ group, wherein $R_6$ represents alkyl or aryl, with the compound of formula V

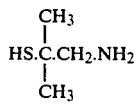

This reaction can be carried out for example by dissolving the compound of formula V in a solution of sodium in an anhydrous lower alcohol e.g. in ethanol or methanol. To this solution is then added a solution of a compound of formula IV in a solvent inert under the reaction conditions e.g. in an aliphatic ketone such as ethylmethylketone or acetone. The reaction proceeds preferably at room temperature up to boiling temperature of the reaction mixture, especially 25° to 55° C.

The starting materials of formula III, IV and V are either known or are preparable analogously to known methods e.g. for compounds V as described in F. J. Carroll, J. D. White and M. E. Wall, J. Org. Chem. 28/1240 (1963).

Alkyl groups appearing as substituents preferably represent lower alkyl groups, especially with 1 to 4 carbon atoms. When $R_2$ stands for a heterocycle then this may contain one or two heteroatoms, whereby one heteroatom is nitrogen and the optionally present second heteroatom is sulphur.

Protecting groups for the amino function in the starting materials of formula III include those commonly used as amino-protecting groups, for example —CO.O.CH$_2$.C$_6$H$_5$(Z), —CO.O.C(CH$_3$)$_3$ (BOC) or —CO.O.CH$_2$CCl$_3$.

Preferred substituent meanings are $R_1 =$
   (a) ethyl
   (b) vinyl whereby vinyl is especially preferred $R_2 =$
   (a) aminoalkyl
   (b) aminohydroxyalkyl
   (c) as (a) or (b) with alkyl having $C_{1-6}$ especially $C_{1-4}$
   (d) 5-membered saturated heterocycle
   (e) 5-membered saturated heterocycle containing one N atom and optionally one S atom.

Combinations of these groups are especially preferred.

A particularly preferred individual compound is 14-O-[1(2-Amino-3-methyl-butyrylamino)-2-methyl-propan-2-yl-thioacetyl]-mutilin as free base or hydrochloride, preferably in (D)-Form.

In the following examples which illustrate the invention but in no way limit its scope, references to temperature are in degrees celsius.

EXAMPLE 1

14-0-[1-((D)-2-Amino-3-methylbutyrylamino)-2-methylpropan-2-yl-thioacetyl]-19,20-dihydromutilin.-Hydrochloride A solution of 1.85 g of Z-Valin-4-nitrophenylester and 2.35 g of 14-0-[(1-Amino-2-methylpropan-2-yl)thioacetyl]-19,20-dihydromutilin in 30 ml of dimethyl formamide is maintained for 7 hours at 25°. The reaction mixture is then poured onto water and repeated shaken with ethylacetate. After washing back the organic phase with 0.1N hydrochloric acid and then with NaCl-saturated water the protected final compound is obtained which can be employed for deprotection without further purification.

A solution of 3.1 g of this Z-protected compound in 150 ml of ethanol is mixed with 60 mg of Pd/active charcoal (palladium on active charcoal, 10%) and stirred under an hydrogen atmosphere for 1 hour. The title compound is obtained in practically quantative yield. The process can also be carried out with BOC-Valin-4-nitro phenylester whereby deprotection is carried out in the following manner. 3 mMol of the BOC-protected compound are dissolved at $-10°$ in 25 ml of trifluoroacetic acid and kept at this temperature for 10 minutes. The reaction mixture is then brought to 25°, allowed to react for a further 2 hours and then poured onto 100 ml of 10% $NaHCO_3$ solution. After repeated extraction with ethylacetate and washing back of the organic phase the crude product is obtained which is chromatographed over silica gel (eluant $CHCl_3/CH_3OH=7/1$).

The following compounds of formula I may be obtained analogously to Example 1.

| Example | $R_1$ | $R_2$ |
|---|---|---|
| 2 | $-CH=CH_2$ | $-CH_2.NH_2$ |
| 3 | " | $-CH.CH_3$ (D)<br>$\|$<br>$NH_2$ |
| 4 | " | $-CH.CH_2.CH.CH_3$<br>$\|$ $\|$<br>$NH_2$ $CH_3$ |
| 5 | $-C_2H_5$ | $-CH.CH_3$ (D)<br>$\|$<br>$NH_2$ |
| 6 | $-CH=CH_2$ | $-CH.CH_3$ (L)<br>$\|$<br>$NH_2$ |
| 7 | " | ⟨S-N(L) ring⟩<br>$\|$<br>$H$ |
| 8 | " | ⟨S-N(L) ring⟩<br>$\|$<br>$H$ |
| 9 | $-C_2H_5$ | $-CH_2CH_2.NH_2$ |
| 10 | $-CH=CH_2$ | $-CH-CH-CH_3$<br>$\|$ $\|$<br>$NH_2$ $CH_3$ (L) |
| 11 | " | ⟨N-H ring⟩ (D) |
| 12 | " | $-CH-CH-CH_3$<br>$\|$ $\|$<br>$NH_2$ $CH_3$ (D) |
| 13 | " | $-CH-CH_2OH$<br>$\|$<br>$NH_2$ (L) |

| | NMR-Spectra ($CDCl_3$) |
|---|---|
| Example | Spectrum |
| 1 | 5.62 (d, 1H, $H_{14}$, $J_{H14H13}$ = 7,5 Hz); 7.72 (t, 1H, NHCO); 3.42 (d, 1H, N—CH—CO, J = 6,25 Hz); 3.32 (d, 1H, $H_{11}$, $J_{H11H10}$ = 6,25 Hz); AB-System: ($V_A$ = 3.17, $V_B$ = 3.27, $J_{AB}$ = 15 Hz, S—$CH_2$—CO). |
| 2 | 7.68 (t, 1H, NH); 5.73 (d, 1H, $H_{14}$, $J_{H14H13}$ = 8,75 Hz); 3.75 (s, 2H, CO—$CH_2$—$NH_2$); 3.38 (d, 1H, $H_{11}$, $J_{H11H10}$ = 6,25 Hz); 3.28 (m, 2H, ≡C—$CH_2$—NH); 1.25, 1.26 (s, s, 6H, gem. $CH_3$). |
| 3 | 7.78 (t, 1H, NH); 5.74 (d, 1H, $H_{14}$, $J_{H14H13}$ = 8,75 Hz); 4.03 (q, 1H, —CH—$CH_3$, J = 7,5 Hz); 3.37 (d, 1H, $H_{11}$, $J_{H11H10}$ = 6,25 Hz); 1.25 (s, 2 × $CH_3$, gem. $CH_3$); 3.3 (m, 2H, ≡C—$CH_2$—NH). |
| 4 | 7.76 (t, 1H, NH); 5.76 (d, 1H, $H_{14}$, $J_{H14H13}$ = 8,75 Hz); $CH_2$<br>$\|$<br>3.43 (dd, 1H, CO—CH—$NH_2$, J = 3,75 Hz, J' = 8,75 Hz); 3.25 (d, 2H, CH—$CH_2$—$NH_2$); AB-System; ($V_A$ = 3.17, $V_B$ = 3.25; $J_{AB}$ = 15 Hz, —S—$CH_2$CO). |
| 5 | 5.64 (d, 1H, $H_{14}$, $J_{H14J13}$ = 8,1 Hz); 3.56 (q, 1H, $CH_3$—CH, J = 7,5 Hz); 3.44 (d, 1H, $H_{11}$, $J_{H11H10}$ = 6,25 Hz); AB-System: ($V_A$ = 3.17, $V_B$ = 3.25, $J_{AB}$ = 15 Hz, S—$CH_2$—CO); ABX-System: ($V_A$ = 3.33, $V_B$ = 3.25, $V_X$ = 7.75, $J_{AB}$ = 13,4 Hz, $J_{AX}$ = $J_{BX}$ = 7,5 Hz, C—$CH_2$—NH). |
| 6 | 7.74 (t, 1H, NH); 5.75 (d, 1H, $H_{14}$, $J_{H14H13}$ = 8,75 Hz); $CH_3$<br>$\|$<br>3.56 (q, 1H, CO—CH—NH, J = 7,5 Hz); 3.36 (d, 1H, $H_{11}$, $J_{H11H10}$ = 6,25 Hz); AB-System: ($V_A$ = 3.17, $V_B$ = 3.24, $CH_3$<br>$\|$<br>$J_{AB}$ = 15 Hz, S—$CH_2$—CO); 1.4 (d, 3H, CO—CH—$NH_2$, J = 7,5 Hz). |
| 7 | 7.72 (t, 1H, NH); 5.77 (d, 1H, $H_{14}$, $J_{H14H13}$ = 8,75 Hz); AB-System: ($V_A$ = 4.29, $V_B$ = 4.13, $J_{AB}$ = 10 Hz, S—$CH_2$—NH); 3.36 (m, 1H, $H_{11}$). |
| 8 | 8.07 (m, 1H, NH); 5.76 (d, 1H, $H_{14}$, $J_{H14J13}$ = 8,75 Hz); $CH_2$<br>$\|$<br>3.84 (dd, 1H, CO—CH—NH, J = 5 Hz, J' = 8,75 Hz); 3.38 (d, 1H, $H_{11}$, $J_{H11H10}$ = 6,25 Hz); AB-System: ($V_A$ = 3.17, $V_B$ = 3.25, $J_{AB}$ = 15 Hz, S—$CH_2$—CO); 3.25 (m, 2H, ≡C—$CH_2$—NH). |
| 9 | 5.62 (d, 1H, $H_{14}$, $J_{H14H13}$ = 7,5 Hz); 3.24 (d, 1H, $H_{11}$, $J_{H11H10}$ = 6,25 Hz); ABX-System: ($V_A$ = 3.34, $V_B$ = 3.26, $V_X$ = 7.38, $J_{AB}$ = 13,5 Hz, $J_{AX}$ = $J_{BX}$ = 7,5 Hz, NH—$CH_2$—C≡); 3.83 (t, 2H, $NH_2$—$CH_2$, J = 5 Hz); 2.38 (t, 2H, $CH_2$CO, J = 5 Hz). |
| 10 | 7.68 (m, 1H, NH); 5.74 (d, 1H, $H_{14}$, $J_{H14H13}$ = 8,75 Hz); 3.2 (s, 2H, S—$CH_2$—CO); 3.38 (m, 1H, $H_{11}$); 3.25 (d, 1H, CH—$CH_3$, J = 3,75 Hz). |
| 11 | 8.05 (t, 1H, NH, NH—$CH_2$—C≡); 5.73 (d, 1H, $H_{14}$, $CH_2$<br>$\|$<br>$J_{H14H13}$ = 8,75 Hz); 4.48 (dd, 1H, NH—CH—CO, J = 8,75, J' = 6,25); 1.25, 1.22 (s, s, mixed $CH_3$); AB System: ($V_A$ = 3.18, $V_B$ = 3.24, $J_{AB}$ = 15 Hz, S—$CH_2$—CO). |
| 12 | 7.8 (m, 1H, NH); 5.75 (d, 1H, $H_{14}$, $J_{H14H13}$ = 8,75 Hz); 3.38 (d, 1H, $H_{11}$, $J_{H11H10}$ = 6,25 Hz); 3.24 (d, 1H, CH—$NH_2$); 3.2 (s, 2H, S—$CH_2$—CO); 3.31 (m, 2H, $CH_2$—NHCO). |
| 13 | 7.9 (m, 1H, NH); 5.75 (d, 1H, $H_{14}$, $J_{H14H13}$ = 8,75 Hz); AB-System: ($V_A$ = 3,18, $V_B$ = 3,28, $J_{AB}$ = 15 Hz, S—$CH_2$—CO); 3.36 (m, 1H, $H_{11}$); 3.91 (dd, 1H, —CHH'—OH, $J_1$ = 10 Hz, $J_2$ = 5 Hz); 3.71 (dd, 1H, —CHH'—OH, $J_1$ = 10 Hz, $J_2$ = 6,25 Hz); 3.5 (dd, 1H, $NH_2$—CH—$CH_2$, $J_1$ = 6,25 Hz, $J_2$= 5 Hz). |

The 14-0-[(1-Amino-2-methylpropan-2-yl)thioacetyl]-19,20-dihydromutilin required as starting material may be obtained as follows. 4.6 g of sodium are dissolved in 500 ml of ethanol (absolute), mixed with 14.1 g of 3-amino-2-methyl-2-propyl merceptane [F. I. Carroll, J. D. White, M. E. Wall, J. Org. Chem. 28, 1240 (1963)] and stirred for one hour at 25°. The reaction mixture is then mixed with a solution of 53.2 g of 19,20- dihydro-pleuromutilin-22-0-tosylate in 300 ml of ethylmethylketone and maintained at 25° for 15 hours. The reaction mixture is poured onto ice-water and repeatedly extracted with ethylacetate. After washing back the organic phase with NaCl-saturated water, the crude product is obtained which is chromatographed over silicagel (eluant: $CHCl_3/CH_3OH = 7/1$).

NMR ($CDCl_3$): 5.8 (d, 1H, $H_{14}$, $J_{H14H13}=9$ Hz); 3.38 (d, 1H, $H_{11}$, $J_{H11H10}=6,3$ Hz); 3.17 (s, 2H, S—CH$_2$—CO); 2.65 (s, 2H, N—CH$_2$—C≡); 1.7 (b, 2H, NH$_2$); 1.28 (s, 6H, 2×CH$_3$).

We claim:
1. A compound of formula I wherein
R$_1$ represents ethyl or vinyl and
R$_2$ represents thiazolidin-4-yl, pyrrolidin-2-yl or aminoalkyl having from 1 to 6 carbon atoms, which is unsubstituted or substituted in its alkyl moiety by hydroxy, in free form or in the form of a physiologically acceptable acid addition or quaternary salt.

2. A compound of claim 1 which is selected from 14-0-[1-((D-2-amino-3-methylbutyrylamino)-2-methylpropan-2-yl-thioacetyl]-19,20-dihydromutilin; 14-0-[1-(aminoacetylamino)-2-methylpropan-2-yl-thioacetyl]-mutilin; 14-0-[1-((D)-2-aminopropionylamino)-2-methylpropan-2-yl-thioacetyl]-mutilin; 14-0-[1-(2-amino-4-methylvalerylamino)-2-methylpropan-2-yl-thioacetyl]-mutilin; 14-0-[1-((D)-2-aminopropionylamino)-2-methylpropan-2-yl-thioacetyl]-19,20-dihydromutilin; 14-0-[1-((L)-2-aminopropionylamino)-2-methylpropan-2-yl-thioacetyl]-mutilin; 14-0-[1-((L)-thiazolidin-4-yl-carbonylamino)-2-methylpropan-2-yl-thioacetyl]-mutilin; 14-0-[1-((L)-pyrrolidin-2-yl-carbonylamino)-2-methylpropan-2-yl-thioacetyl]-mutilin; 14-0-[1-(3-aminopropionylamino)-2-methylpropan-2-yl-thioacetyl]-19,20-dihydromutilin; 14-0-[1-((L)-2-amino-3-methylbutyrylamino)-2-methylpropan-2-yl-thioacetyl]-mutilin; 14-0-[1-((D)-pyrrolidin-2-yl-carbonylamino)-2-methylpropan-2-yl-thioacetyl]-mutilin; in free form or in the form of a physiologically acceptable acid addition or quaternary salt.

3. A compound according to claim 1 wherein R$_1$ is vinyl and R$_2$ is aminohydroxyalkyl.

4. A compound according to claim 1 wherein R$_1$ is vinyl and R$_2$ is thiazolidin-4-yl, pyrrolidin-2-yl or unsubstituted aminoalkyl and if containing an asymmetric carbon atom is in (D)-Form.

5. A compound of claim 1 which is 14-0-[1-((D)-2-amino-3-methylbutylamino)-2-methylpropan-2-yl-thioacetyl]-mutilin, in free form or in the form of a physiologically acceptable acid addition or quaternary salt.

6. A compound of claim 1 which is 14-0-[1-((L)-2-amino-3-hydroxypropionylamino)-2-methylpropan-2-yl-thioacetyl)-mutilin, in the form of a physiologically acceptable acid addition or quaternary salt.

7. A compound of claim 1 in which R$_1$ is vinyl.

8. A compound of claim 1 in which R$_2$ is thiazolidin-4-yl or pyrrolidin-2-yl.

9. A compound of claim 4 in which R$_2$ is amino alkyl.

10. The compound wherein R$_1$ is ethyl or vinyl.

11. A chemotherapeutic composition comprising a compound according to claim 1 in free base or chemotherapeutically acceptable acid addition or quaternary salt form in an amount effective in combatting bacteria and obligatory anaerobes together with a chemotherapeutically acceptable diluent or carrier.

12. A feed or drinkwater additive composition comprising a compound according to claim 1, in free base or physiologically acceptable acid addition or quaternary salt form in an amount effective for the prophylaxis or therapy of microorganism infections and for growth promotion in domestic animals together with a physiologically acceptable diluent or carrier.

13. A composition of claim 12 in which the amount of compound is from 0.0125 to 0.05 weight by volume in drinking water.

14. A composition of claim 12 in which the amount of compound is from 20 to 400 grams/metric ton of foodstuff.

15. A composition of claim 12 in which the amount of compound is from 0.0125 to 0.025 weight by volume in drinking water.

16. A composition of claim 12 in which the amount of compound is from 20 to 200 grams/metric ton of feedstuff.

17. A composition of claim 11 in which the amount of compound is from about 250 mg to 1500 mg.

18. A method of combatting bacteria and obligatory anerobes comprising administering to a subject in need of such treatment an amount of a compound according to claim 1 in free form or in the form of a chemotherapeutically acceptable acid addition or quaternary salt thereof effective in combatting bacteria and obligatory anaerobes.

19. A method of combatting microorganism infections and promoting growth in domestic animals which comprses administering to an animal in need of such treatment a compound according to claim 2 in free form or in the form of a physiologically acceptable acid addition or quaternary salt thereof in an amount effective in combatting microorganism infections and promoting growth in domestic animals.

20. A method of claim 18 in which the amount of compound is from 1 gram to 3 grams per day.

* * * * *

UNITED STATES PATENT AND TRADEMARK OFFICE
CERTIFICATE OF CORRECTION

PATENT NO. : 4,675,330

DATED : June 23, 1987

INVENTOR(S) : Heinz Berner and Hermann Vyplel

It is certified that error appears in the above-identified patent and that said Letters Patent is hereby corrected as shown below:

Column 7, lines 56 and 66 and column 8, line 2, cancel "or quaternary". Column 7, line 63, "methylbutylamino)" should read "methylbutyrylamino". Column 8, line 61, "2" should read "1".

Signed and Sealed this

Twenty-ninth Day of December, 1987

Attest:

DONALD J. QUIGG

Attesting Officer   Commissioner of Patents and Trademarks